(12) United States Patent
Choi et al.

(10) Patent No.: US 12,390,144 B2
(45) Date of Patent: Aug. 19, 2025

(54) NEURAL SIGNAL FEEDBACK SYSTEM AND METHOD USING MICROELECTRODE ARRAY UNIT

(71) Applicant: UIF (University Industry Foundation), Yonsei University, Seoul (KR)

(72) Inventors: Heon Jin Choi, Seoul (KR); Jae Suk Sung, Suwon-si (KR)

(73) Assignee: UIF (UNIVERSITY INDUSTRY FOUNDATION), YONSEI UNIVERSITY, Seoul (KR)

(*) Notice: Subject to any disclaimer, the term of this patent is extended or adjusted under 35 U.S.C. 154(b) by 699 days.

(21) Appl. No.: 17/337,705

(22) Filed: Jun. 3, 2021

(65) Prior Publication Data

US 2021/0401351 A1    Dec. 30, 2021

(30) Foreign Application Priority Data

Jun. 30, 2020  (KR) ........................ 10-2020-0079786

(51) Int. Cl.
*A61B 5/294*  (2021.01)
*A61B 5/00*  (2006.01)
(Continued)

(52) U.S. Cl.
CPC ............ *A61B 5/388* (2021.01); *A61B 5/0002* (2013.01); *A61B 5/24* (2021.01); *A61B 5/294* (2021.01);
(Continued)

(58) Field of Classification Search
CPC ....... A61B 5/388; A61B 5/294; A61B 5/0002; A61B 5/24; A61B 5/311;
(Continued)

(56) References Cited

U.S. PATENT DOCUMENTS

| 2003/0166996 A1* | 9/2003 | Kim ........................ A61B 5/16 600/300 |
| 2006/0009691 A1* | 1/2006 | Yeo ...................... A61B 5/0245 600/521 |

(Continued)

FOREIGN PATENT DOCUMENTS

KR  10-2005-0046957   5/2005
KR  10-2020-0027417   3/2020

*Primary Examiner* — Joanne M Rodden
*Assistant Examiner* — Dana Stumpfoll
(74) *Attorney, Agent, or Firm* — LEX IP MEISTER, PLLC

(57) ABSTRACT

Disclosed herein are a neural signal feedback system and method. The neural signal feedback system includes: a microelectrode array unit configured such that a plurality of microelectrodes is disposed on a substrate and such that one microelectrode, which is a reference electrode, and corresponding electrode groups including other microelectrodes located at different same distances from the reference electrode are set; and an analysis and determination unit configured to compare neural signal values, measured in the microelectrode array unit, with a preset reference value, and to determine whether to apply the electrical stimulation of the microelectrode array unit. The analysis and determination unit performs re-measurement after the application of electrical stimulation, and repeats the application of electrical stimulation and measurement until the measured values reach the reference value.

6 Claims, 14 Drawing Sheets

(51) Int. Cl.
*A61B 5/24* (2021.01)
*A61B 5/311* (2021.01)
*A61B 5/388* (2021.01)

(52) U.S. Cl.
CPC ....... *A61B 5/311* (2021.01); *A61B 2562/0209* (2013.01); *A61B 2562/046* (2013.01); *A61B 2562/166* (2013.01)

(58) Field of Classification Search
CPC ...... A61B 2562/0209; A61B 2562/046; A61B 2562/166; A61B 2562/028; A61N 1/36132; A61N 1/05; A61N 1/36135
See application file for complete search history.

(56) References Cited

U.S. PATENT DOCUMENTS

| | | | |
|---|---|---|---|
| 2007/0167859 A1* | 7/2007 | Finneran | A61B 5/296 600/546 |
| 2012/0245436 A1* | 9/2012 | Rutkove | A61B 5/053 600/301 |
| 2012/0277834 A1* | 11/2012 | Mercanzini | A61N 1/36125 607/116 |
| 2014/0243926 A1* | 8/2014 | Carcieri | A61N 1/36071 607/46 |
| 2015/0257687 A1* | 9/2015 | Pushpala | A61B 5/01 600/345 |
| 2016/0278672 A1* | 9/2016 | Cho | A61B 5/1473 |
| 2019/0239763 A1* | 8/2019 | Block | A61B 5/6814 |

* cited by examiner

A

NEURAL SIGNAL FEEDBACK SYSTEM AND METHOD USING MICROELECTRODE ARRAY UNIT

CROSS-REFERENCE TO RELATED APPLICATION

This application claims the benefit of Korean Patent Application No. 10-2020-0079786 filed on Jun. 30, 2020, which is hereby incorporated by reference herein in its entirety.

BACKGROUND

1. Technical Field

The present invention relates generally to a neural signal feedback system and method, and more particularly to a neural signal feedback system and method using a microelectrode array unit.

2. Description of the Related Art

The present invention relates to a method of introducing an accurate measurement and semantic analysis method using a neural signal feedback system that utilizes a neuron information amount algorithm, and treating a nerve-related problem.

Various methods are being researched to accurately measure neural bio-signals. To this end, a biological signal is measured through an ultra-precision electrode such as a nano-electrode. In addition, research is being conducted into a method of reducing pain and treating a nerve-related problem by applying predetermined stimulation around a nerve.

As a conventional art, there is a product called a signal cord stimulator (SCS) that applies stimulation to the nervous system. This is a product that reduces the pain of a patient by applying electrical stimulation near the nervous system.

Current technology uses a method of performing partial anesthesia only on a treatment target site and, while talking with a patient, applying desired electrical stimulation to various places near the nervous system, checking a part in which pain is most effectively reduced, and then applying stimulation to the part.

However, the current technology is problematic in that an accurate problematic area cannot be found and in that stimulation is applied to a region not requiring stimulation because excessive stimulation is applied to an approximate problematic area.

In addition, the current technology causes inconvenience in that a patient must visit a hospital and a doctor's procedure is required at each visit.

RELATED ART DOCUMENTS

Patent document 1: Korean Patent Application Publication No. 10-2017-0072018 (published on Jun. 26, 2017)
Patent document 2: Korean Patent Application Publication No. 10-2019-0034867 (published Apr. 3, 2019)

SUMMARY

A neural signal feedback system and method using a microelectrode array unit according to the present invention have the following objects:

A first object of the present invention is to accurately measure the bio-signal of a correct area by utilizing a microelectrode structure. To this end, the present invention is intended to propose a simple and highly-accurate microelectrode array pattern structure and acquire a number of measured values using the microelectrode array pattern structure.

A second object of the present invention is to, in order to accurately measure and analyze a bio-signal, convert an analog bio-signal into a digital signal and analyze a measured value more accurately.

A third object of the present invention is to determine whether to apply electrical stimulation by analyzing an accurately measured bio-signal and then comparing it with existing reference value data.

A fourth object of the present invention is to construct a feedback system that automatically applies electrical stimulation.

The objects of the present invention are not limited to those mentioned above, and other objects that are not mentioned above will be clearly understood by those skilled in the art from the following description.

According to an aspect of the present invention, there is provided a neural signal feedback system, the neural signal feedback system being operated by a program executed by an operation processing means including a computer, the operation processing means including an analysis and determination unit, the neural signal feedback system including: a microelectrode array unit configured such that a plurality of microelectrodes is disposed on a substrate and such that one microelectrode, which is a reference electrode, and corresponding electrode groups including other microelectrodes located at different same distances from the reference electrode are set; and the analysis and determination unit configured to compare neural signal values, measured in the microelectrode array unit, with a preset reference value, and to determine whether to apply the electrical stimulation of the microelectrode array unit; wherein the analysis and determination unit performs re-measurement after the application of electrical stimulation, and repeats the application of electrical stimulation and measurement until the measured values reach the reference value.

The measured neural signal values may include action potential values.

The neural signal values may be converted from an analog signal into a digital signal, and may be expressed as the amounts of information in bits.

The measurement and the application of electrical stimulation may be performed with the individual microelectrodes matched with respective single cells in a one-to-one correspondence.

The analysis and determination unit may receive the measured neural signal values via a wireless or wired connection.

The average of measured values may be obtained for each of the corresponding electrode groups.

The average of measured values excluding at least one of upper and lower limit values of measured values for each of the corresponding electrode groups may be obtained.

The plurality of microelectrodes may be disposed with the same numbers of microelectrodes arranged in the longitudinal and transverse directions, and the reference electrode may be any one of the plurality of microelectrodes.

The plurality of microelectrodes may be disposed with the same odd numbers of microelectrodes arranged in the longitudinal and transverse directions, and the reference electrode may be set to a microelectrode located at the center.

The plurality of microelectrodes may be disposed with different numbers of microelectrodes arranged in the longitudinal and transverse directions, and the reference electrode may be any one of the plurality of microelectrodes.

The plurality of microelectrodes may be disposed at the center of a plurality of concentric circles and on the circumferences of the concentric circles, a reference electrode may be a microelectrode disposed at the center of the circles, and corresponding electrode groups may each be microelectrodes disposed on the circumference of each of the concentric circles.

The plurality of microelectrodes disposed on the substrate may be divided into a plurality of preset sections; and the microelectrodes of each of the preset sections may be configured to detect a different material.

According to another aspect of the present invention, there is provided a neural signal feedback method using a microelectrode array unit, the neural signal feedback method including: measuring, by a microelectrode array unit in which a plurality of microelectrodes is disposed on a substrate and one microelectrode, which is a reference electrode, and corresponding electrode groups including other microelectrodes located at different same distances from the reference electrode are set, neural signal values in a state of having been inserted into the human body, and transmitting, by the microelectrode array unit, the measured values to an analysis and determination unit in the state; determining, by the analysis and determination unit, whether to apply electrical stimulation by comparing the measured values with a preset reference value; and applying, by the analysis and determination unit, electrical stimulation from the microelectrode array unit when, as a result of the comparison, it is determined that the measured values do not reach the reference value; wherein the above steps are repeatedly performed until the measured values reach the reference value; and wherein when the measured values reach the reference value, the analysis and determination unit does not apply electrical stimulation.

The measured neural signal values may include action potential values.

The neural signal values may be converted from an analog signal into a digital signal, and may be expressed as the amounts of information in bits.

The electrical stimulation may be applied through each of the microelectrodes.

According to still another aspect of the present invention, there is provided a computer program stored in a computer-readable recording medium in order to be combined with the hardware of a computer and execute the neural signal feedback method using a microelectrode array unit.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Figure 1:
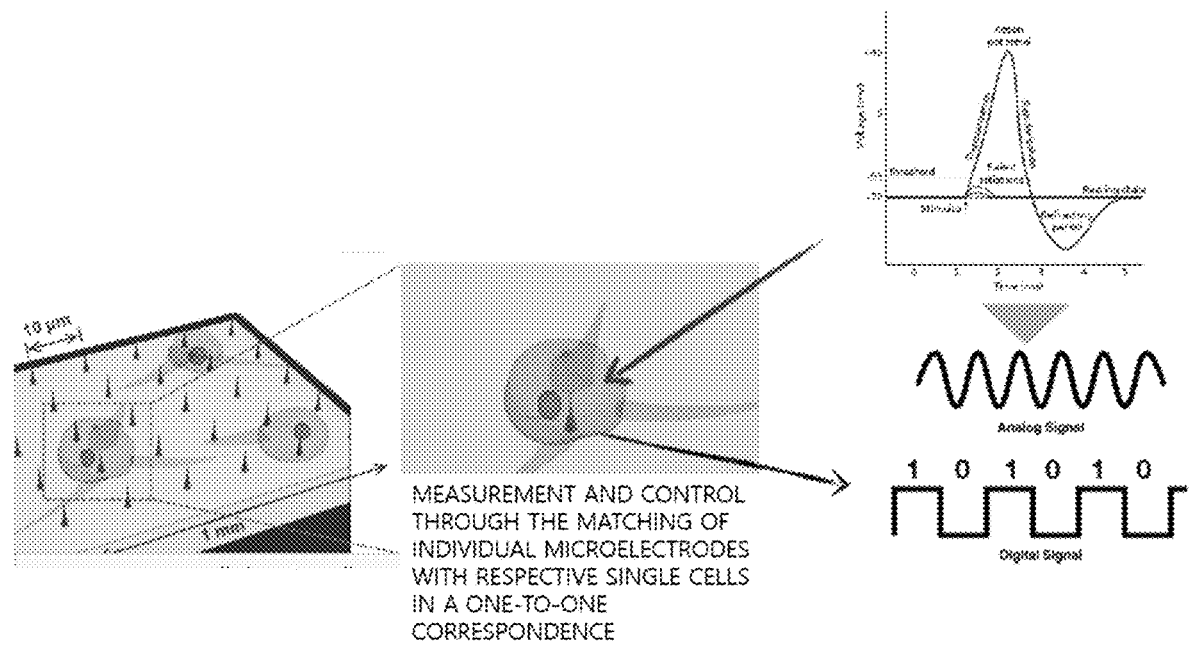
FIG. 1 is a schematic diagram showing a state in which the microelectrode array unit of a neural signal feedback system according to the present invention analyzes a neural signal.
Figure 2:
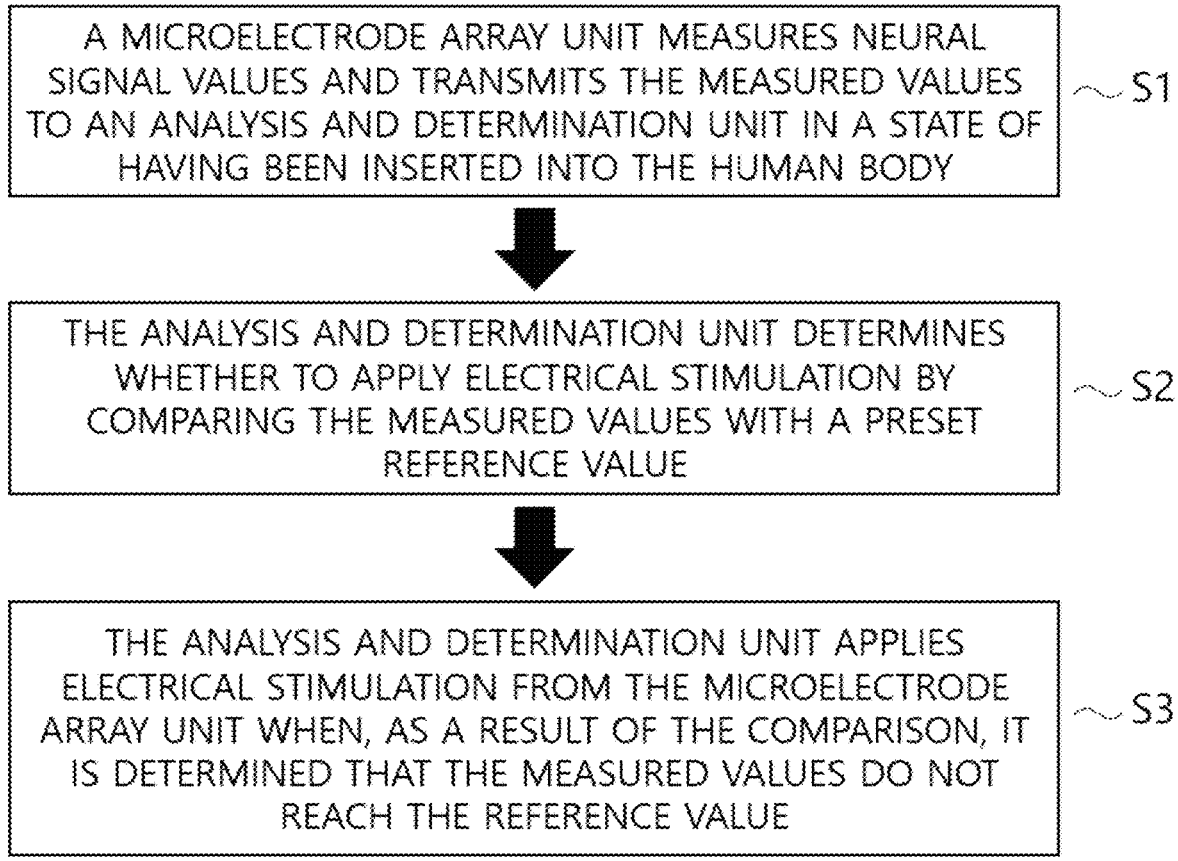
FIG. 2 shows a neural signal feedback method using a microelectrode array unit according to the present invention.
Figure 3:
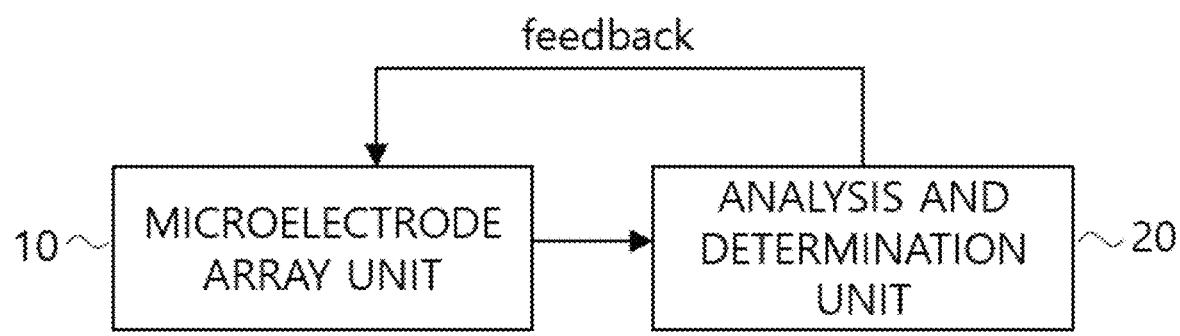
FIG. 3 is a diagram showing the configuration of a neural signal feedback system using a microelectrode array unit according to the present invention.

Embodiments of the present invention will be described in detail below with reference to the accompanying drawings so that those of ordinary skill in the art can easily implement the present invention. As can be easily understood by those of ordinary skill in the art to which the present invention pertains, the following embodiments may be modified in various forms without departing from the spirit and scope of the present invention. The same or similar parts are denoted by the same reference symbols throughout the drawings as much as possible.

The terminology used herein is intended merely to refer only to specific embodiments, and is not intended to limit the present invention. The singular forms used herein also include plural forms unless clearly indicated to the contrary.

The term "including" used herein is intended to specify particular features, regions, integers, steps, acts, elements, and/or components, and is not intended to exclude the presence or addition of another specific feature, region, integer, step, action, element, component, and/or a group thereof.

All the terms including technical and scientific terms used herein have the same meanings as commonly understood by those of ordinary skill in the art to which the present invention pertains. The terms defined in the dictionaries are further interpreted as having meanings consistent with the related technical literature and the present disclosure, and are not interpreted in ideal or overly formal senses unless expressly so defined herein.

Hereinafter, the present invention will be described with reference to the drawings. For reference, the drawings may be partially exaggerated in order to describe the features of the present invention. In this case, it is preferable to perform interpretation in light of the overall purport of the present specification.

The present invention is intended to construct a system that automatically provides feedback on three stages of a bio-signal: measurement, analysis, and stimulation. When a device in which the feedback system according to the present invention is implemented is inserted into the body and operated, it may be possible to administer treatment that automatically applies accurate stimulation to a required area.

The present invention may be implemented as a neural signal feedback system, a neural signal feedback method, and a computer program using the same. The embodiments of the present invention include a microelectrode array unit according to the present invention as a common technical feature.

First, the neural signal feedback system according to the present invention will be described.

The present invention is directed to a neural signal feedback system that may be operated by a program that is executed by an operation processing means including a computer. In this case, the operation processing means includes an analysis and determination unit. More specifically, the present invention is directed to a neural signal feedback system including: a microelectrode array unit configured such that a plurality of microelectrodes is disposed on a substrate and such that one microelectrode, which is a reference electrode, and corresponding electrode groups including other microelectrodes located at different same distances from the reference electrode are set; and an analysis and determination unit 20 configured to compare a neural signal value, measured in the microelectrode array unit 10, with a preset reference value and to determine whether to apply the electrical stimulation of the microelectrode array unit 10.

The analysis and determination unit 20 according to the present invention performs re-measurement after the application of electrical stimulation, and may repeat the application of electrical stimulation and measurement until the measured values reach the reference value.

In the present invention, the measured neural signal values preferably include action potential values.

The neural signal values measured according to the present invention may be converted from an analog signal into a digital signal, and may be expressed as the amounts of information in bits.

In the present invention, the measurement and the application of electrical stimulation performed by the microelectrode array unit 10 may be performed with individual microelectrodes matched with respective single cells in a one-to-one correspondence.

The analysis and determination unit 20 according to the present invention may receive the measured neural signal values via a wireless or wired connection. In the case where the measured neural signal values are received in a wireless manner, the device of the neural signal feedback system according to the present invention may include the wireless communication device part (see FIG. 6).

FIG. 1 is a schematic diagram showing a state in which the microelectrode array unit of the neural signal feedback system according to the present invention analyzes a neural signal. In general, a bio-signal from a nerve or the like is represented by an action potential, which has an analog form as shown in FIG. 1.

Microelectrodes are sufficiently small in size to correspond to respective cells, are constructed in an array form, and measure a number of action potentials. In addition, the transmission and meaning of a neural signal are determined by analyzing the correlations between the number of measured action potentials.

In this case, a number of measured action potential values are in analog form, and thus there is a disadvantage in that it is not easy to compare and analyze the potential values. Accordingly, the present invention is characterized in that all the measured values of the bio-signal in an analog form are converted into the digital signal values "0" and "1," and are then compared and analyzed.

The accurate transmission of a bio-signal may be determined by converting such bio-signal values into digital signal values and expressing the information transmitted by the bio-signal over time as the amounts of bit signal information "0" and "1." In order to express a digital bio-signal as the amounts of bit signal information, Shannon's theory of information and communication may be utilized.

Biological data information according to the present invention may be used for a method of checking whether information transmitted between information sent from numerous neurons and information received is semantic information.

The amounts of information in bits may be measured by converting numerous analog signal values generated by neurons into digital signal values. The present invention is characterized in that the amount of information to be transmitted and the amount of information received are compared with each other and, if the compared amounts of information are the same, it is determined that appropriate semantic information has been transmitted.

As described above, after an analog bio-signal has been converted into a digital signal, the bio-signal may be accurately analyzed and compared by incorporating the information and communication theory thereinto.

Figure 4:
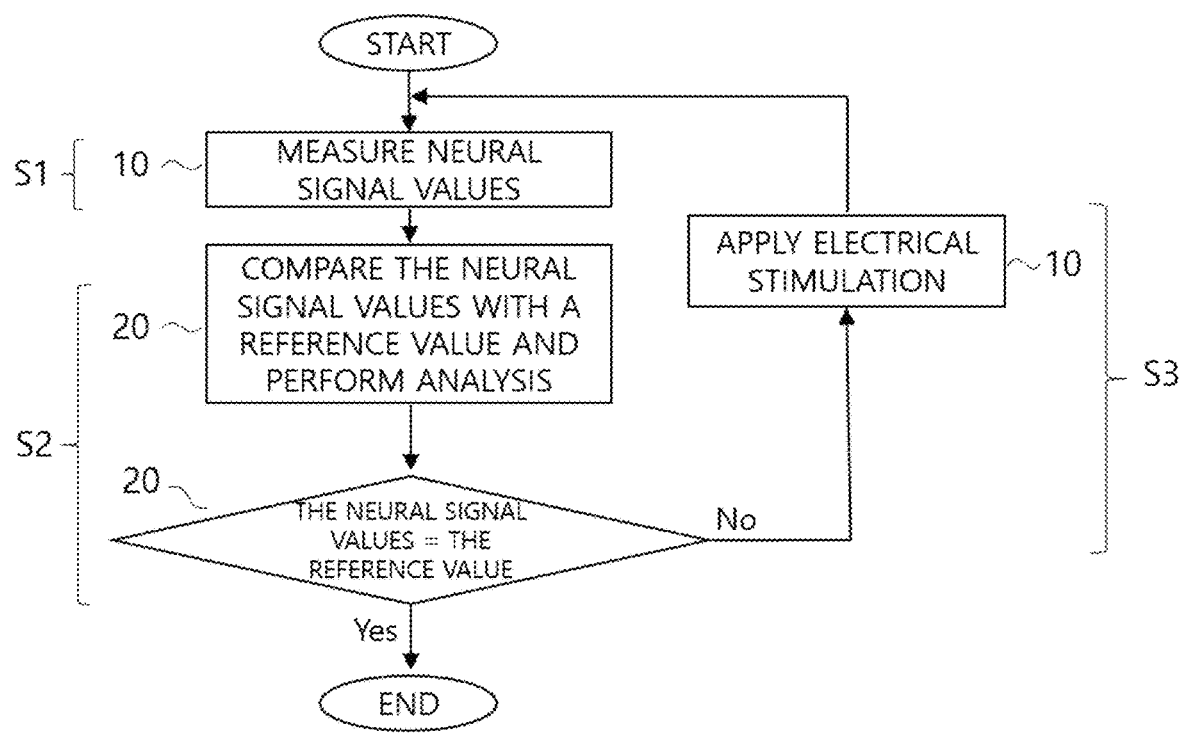
FIG. 4 is a flowchart showing a neural signal feedback method using a microelectrode array unit according to the present invention.

FIG. 4 is a flowchart showing a neural signal feedback method using a microelectrode array unit according to the present invention.

As shown in FIG. 4, the measurement and recording of a neural signal through the device are performed first. There is repeated the process of accurately analyzing the measured neural signal, comparing the measured neural signal with a reference value, which is a neural signal in a normal state, administering treatment to apply stimulation to a nerve if it is different from the data in a normal state, re-measuring a neural signal after the application of the stimulation, and providing feedback while performing analysis and comparison.

In addition, the present invention is characterized by an automatic feedback system that terminates the operation thereof without further neurostimulation treatment if the data values are the same when the measured value is compared with the reference value.

In the past, there has been a simple or partial neural signal measurement or stimulation method. However, there has been no system that performs connection, analysis, and feedback.

One of the main parts of the present invention is a configuration that compares and analyzes neural signals.

As described above, in this analysis configuration, the measured bio-signal is converted into a desired digital form to be suitable for data processing and the amounts of information are measured from the converted data, and thus only significant information is extracted, so that only necessary data directly related to the bio-signal is obtained by removing unnecessary noise components.

The collected data will be collected, converted into big data, and managed through classification.

The classified data may be organized into an algorithm through deep learning and artificial intelligence (AI) techniques. Thereafter, an optimal stimulation treatment plan and the minimum amount of stimulation treatment may be acquired by extracting the correlations between the data organized into the algorithm and the disease or pain of an actual patient.

After this analysis step has been performed, a comparison is made with reference data, which is a normal bio-signal. The fact that the measured and analyzed bio-signal value is the same as the reference value means that there is no abnormality, so that there is no need for treatment such as the application of stimulation.

In contrast, if there is a difference when the measured value is compared with the reference value, it means that there is an abnormality, and thus stimulating treatment may be administered.

There may be automatically repeated a feedback loop in which predetermined stimulation is applied, the step of measuring and analyzing a neural signal again is performed, the measured value is compared with a reference value, and stimulation, measurement, and analysis are performed if the values are still different.

When the measured value of the bio-signal and the reference value are the same through the feedback loop, the feedback loop is terminated without any further iteration.

Through this, when the device is inserted into the human body, a problematic area may be found, and treatment such as the application of stimulation may be automatically administered.

Figure 5:
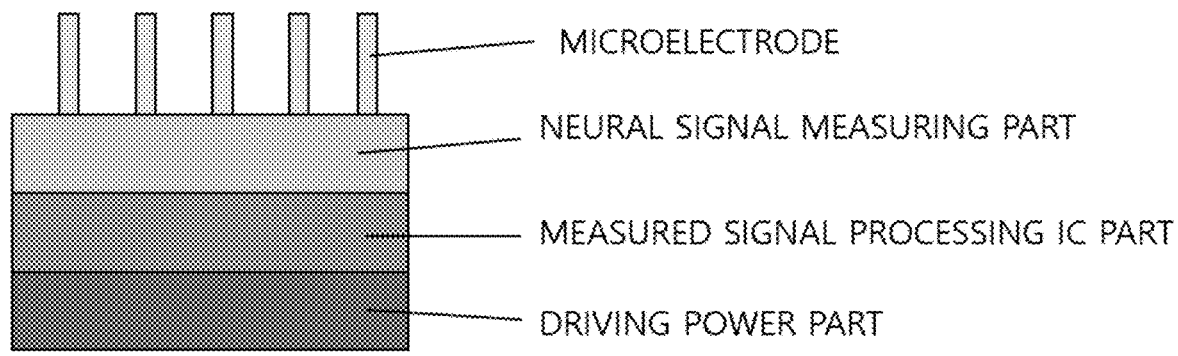
FIGS. 5 and 6 are schematic diagrams showing the configurations of the devices of neural signal feedback systems proposed in the present invention.
Figure 6:
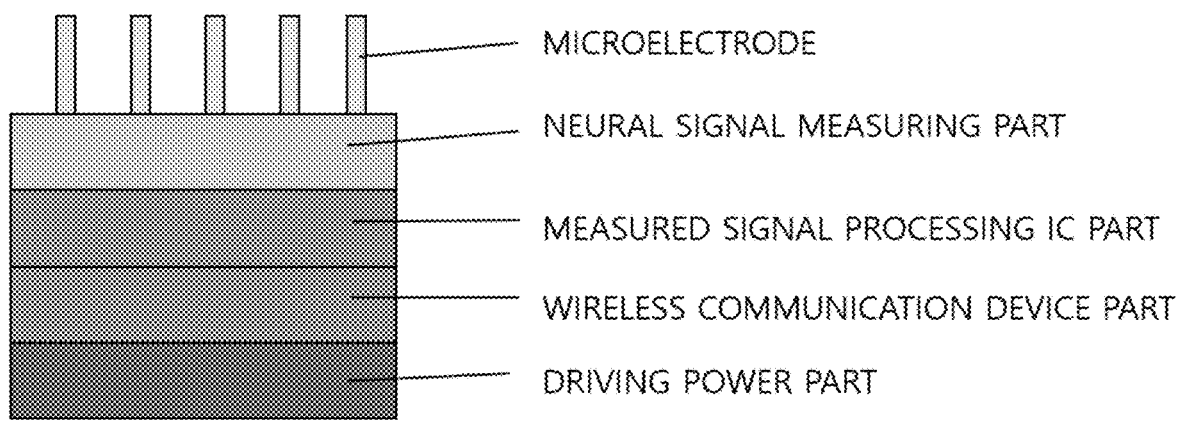

FIGS. 5 and 6 are schematic diagrams showing the configurations of the devices of neural signal feedback systems proposed in the present invention.

FIG. 5 is a schematic diagram showing the configuration of the device of the neural signal feedback system proposed in the present invention. The device includes a neural signal measuring part configured to measure a bio-signal and apply stimulation, and a measured signal processing IC part configured to issue comparison and stimulation commands. In addition, the device further includes a driving power part configured to enable the above operations. Through this structure of the device, a system for measuring and analyzing a biological neural signal and applying stimulation is provided.

FIG. 6 is a schematic diagram showing the configuration of the device of the neural signal feedback system proposed in another embodiment of the present invention. Although the basic configuration of this device is similar to that of FIG. 4, this device may further include a wireless communication device part configured to transmit a measured signal to the outside.

Figure 7:
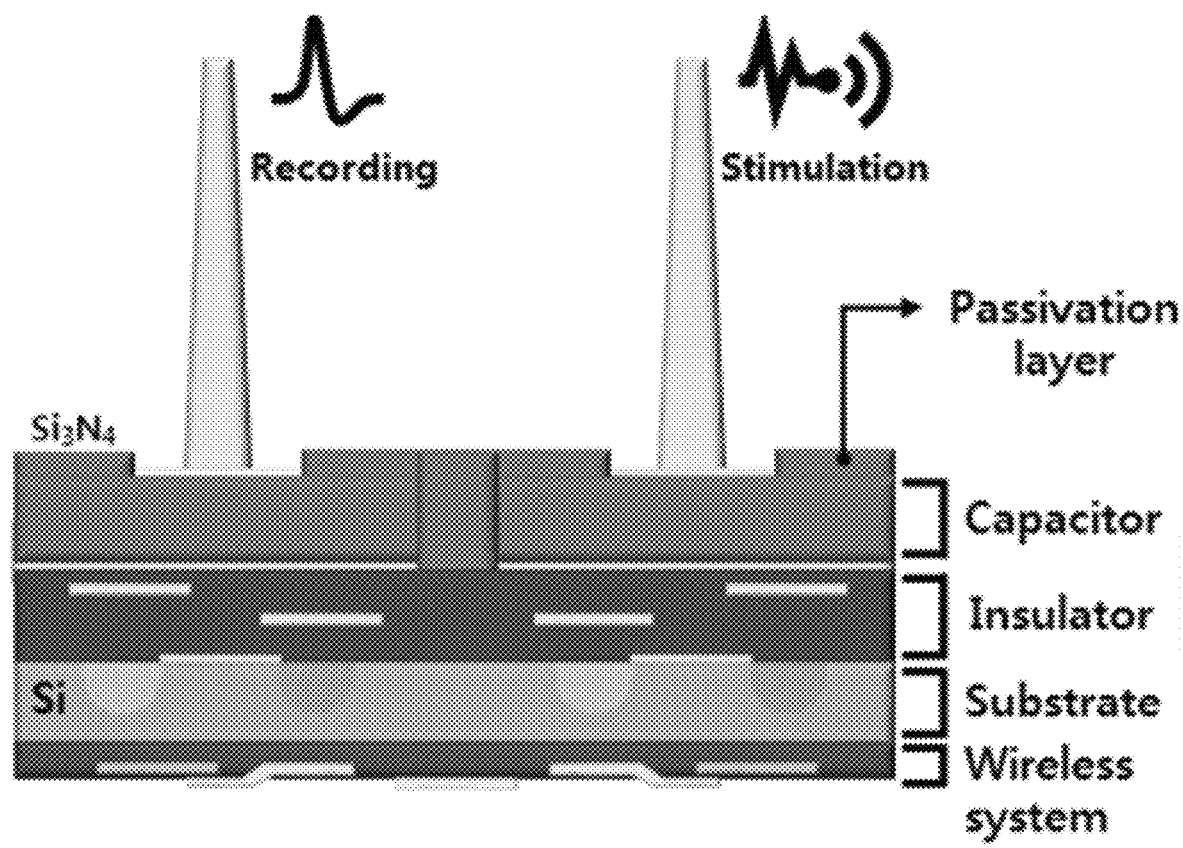
FIG. 7 is a detailed sectional view of the device of a neural signal feedback system proposed in the present invention.
Figure 8:
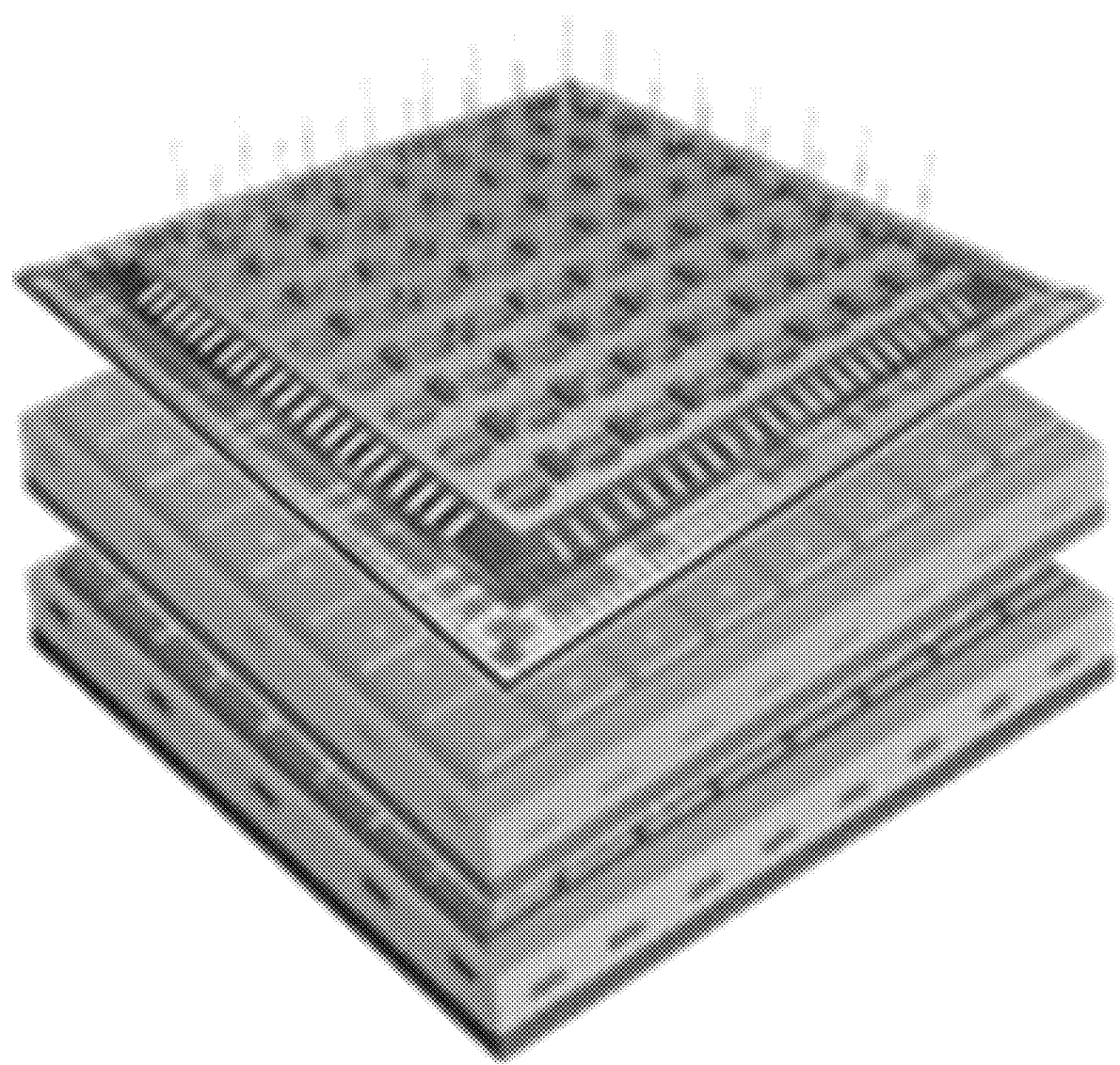
FIG. 8 is a schematic diagram showing the overall configuration of the device of the neural signal feedback system proposed in the present invention.

FIG. 7 is a detailed sectional view of the device of a neural signal feedback system proposed in the present invention. FIG. 8 is a schematic diagram showing the overall configuration of the device of the neural signal feedback system proposed in the present invention.

Next, the array pattern of a microelectrode array unit used in a neural signal feedback system according to the present invention will be described in detail.

In general, in order to detect a disease, an indirect method of detecting a protein generated in vivo due to a disease is used. This protein is called a "biomarker."

A representative biomarker related to cancer is VEGF, and there are various other biomarkers. In addition, there is beta amyloid as a biomarker for Alzheimer's, and there is troponin as a biomarker for myocardial color.

In the case where such a biomarker is provided, when a dielectric characteristic such as dielectric constant in the body and an impedance characteristic such as resistance changes, the presence or absence of a disease is detected by accurately measuring the changes in the dielectric characteristic or impedance characteristic using microelectrodes.

Alternatively, the presence or absence of a disease such as cholera or a heavy metal such as mercury may be determined by observing a change in the dielectric or impedance characteristic between electrodes without a special biomarker.

In this case, what is important is that whether a minute change in the dielectric characteristic or impedance between electrodes is detected means the accuracy of the detection of a disease. In other words, it is of great significance to develop a bio-signal measuring device having high accuracy and high resolution.

Figure 9A:
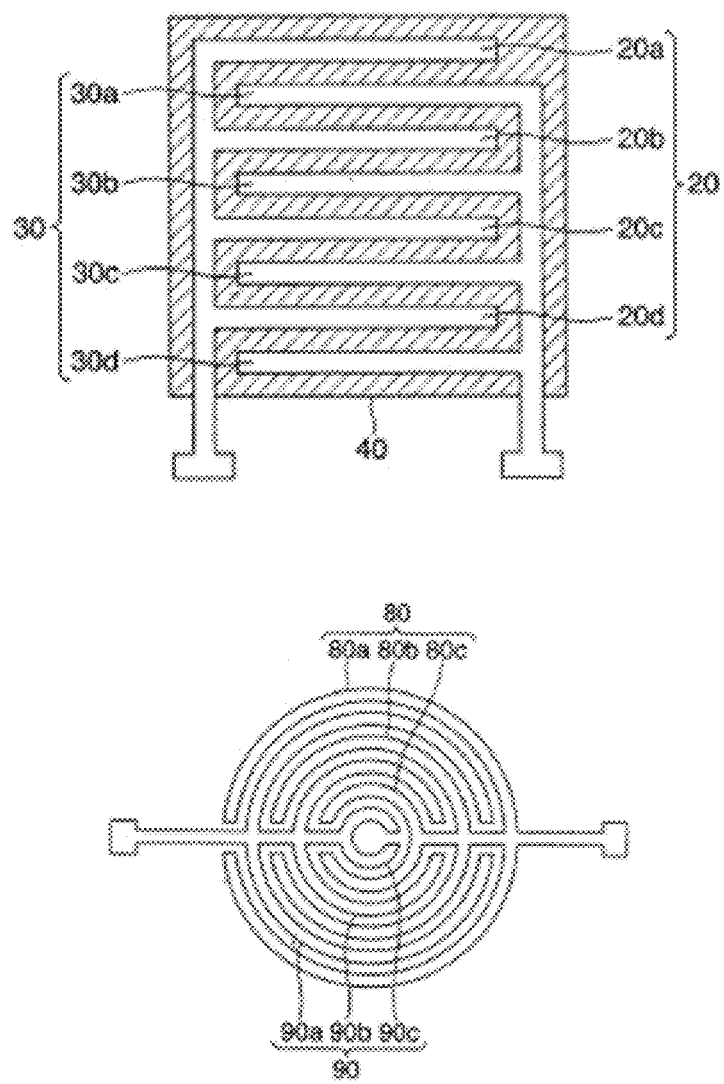
FIG. 9(a) and FIG. 9(b) show structures in which two electrodes are disposed in a conventional bio-signal measuring device.
Figure 9B:
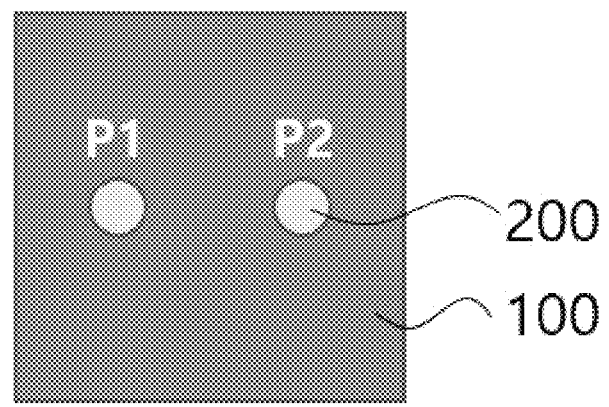
Figure 9B:
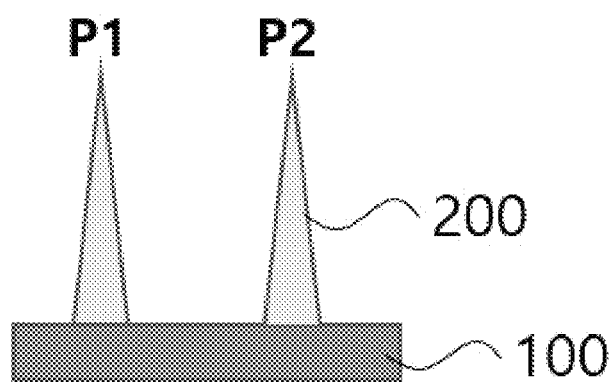

In the conventional art of FIG. 9, only a pair of electrodes are constructed, and thus only one detection is performed by one measurement. Accordingly, in order to increase the reliability of measurement, there is a problem in that a plurality of samples needs to be fabricated and repeated measurement needs to be performed.

In the present invention, in order to overcome the problem, a plurality of array-type electrodes is constructed, and a measuring method is improved.

Meanwhile, the present invention includes both an embodiment in which microelectrodes detect a biomarker and an embodiment in which microelectrodes detect a material other than a biomarker.

Furthermore, the present invention includes both an embodiment in which a receptor that is coupled to a biomarker is provided on the surface of a microelectrode and an embodiment in which a receptor that is coupled to a biomarker is not provided on the surface of a microelectrode. However, the present invention is advantageous in that sufficiently accurate measurement may be performed even when a receptor is not provided on the surface of a microelectrode because the number of measured values is considerably large and thus the accuracy of measurement is considerably high.

The technical configuration of the array pattern of a microelectrode array unit according to the present invention will be described in detail below with reference to the drawings.

Figure 10:
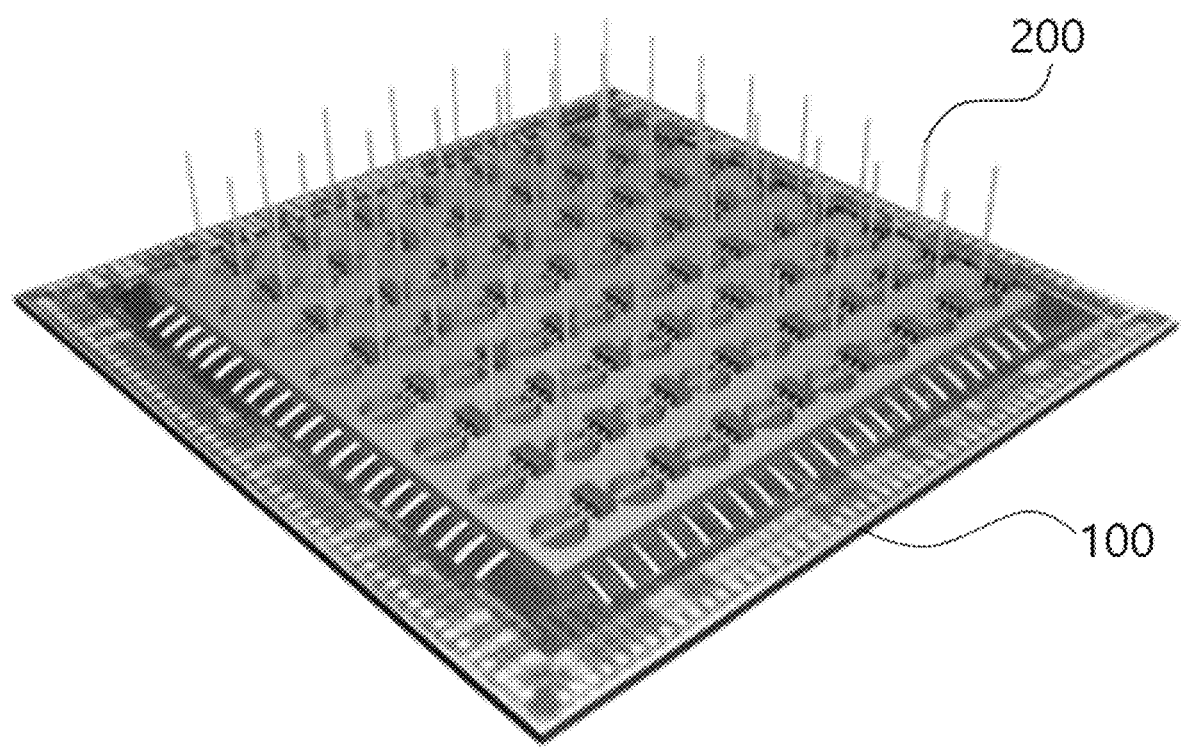
FIG. 10 is a schematic diagram of a microelectrode array pattern according to the present invention.
Figure 11:
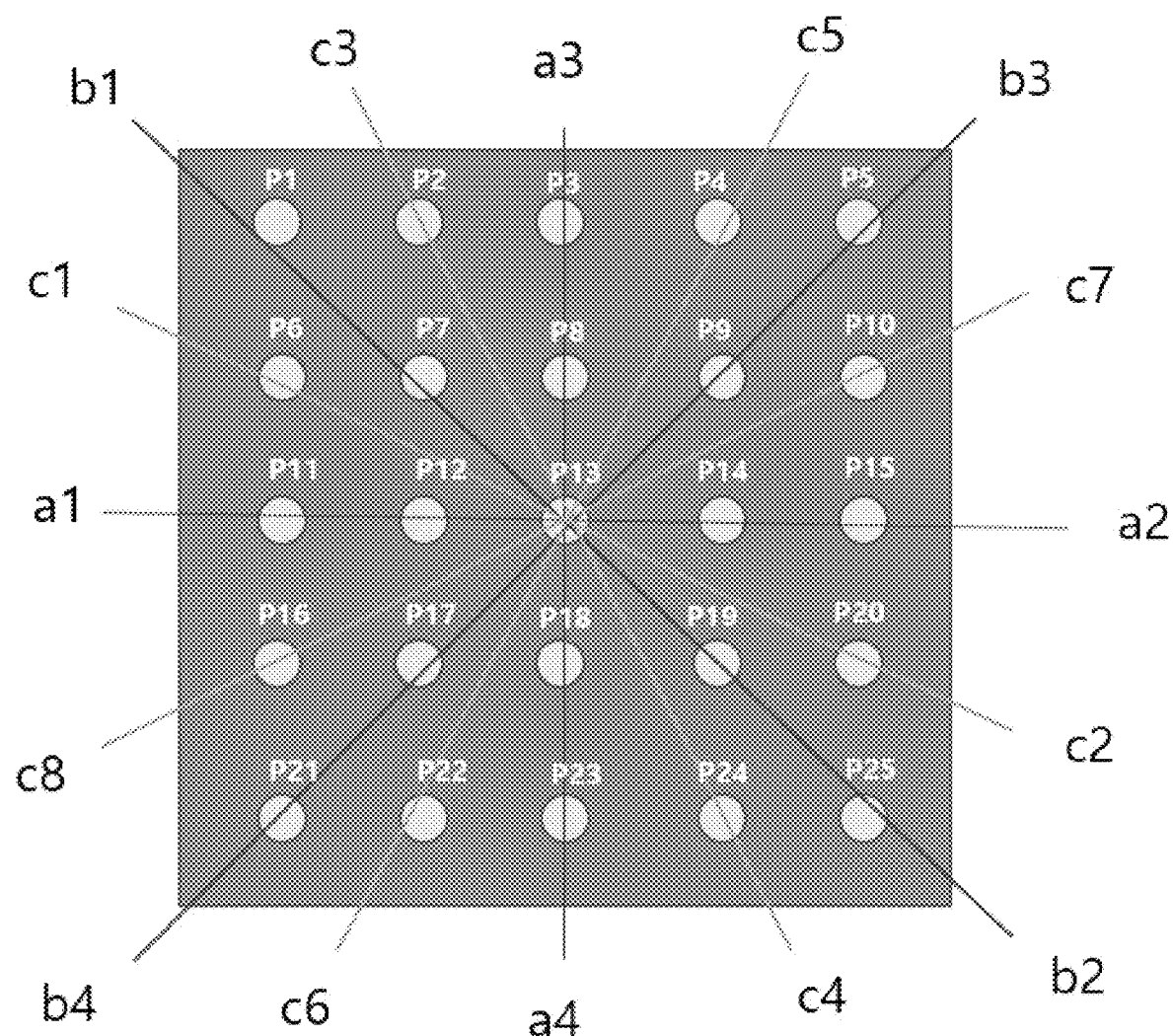
FIGS. 11 to 13 show various embodiments of a microelectrode array pattern according to the present invention.
Figure 12:
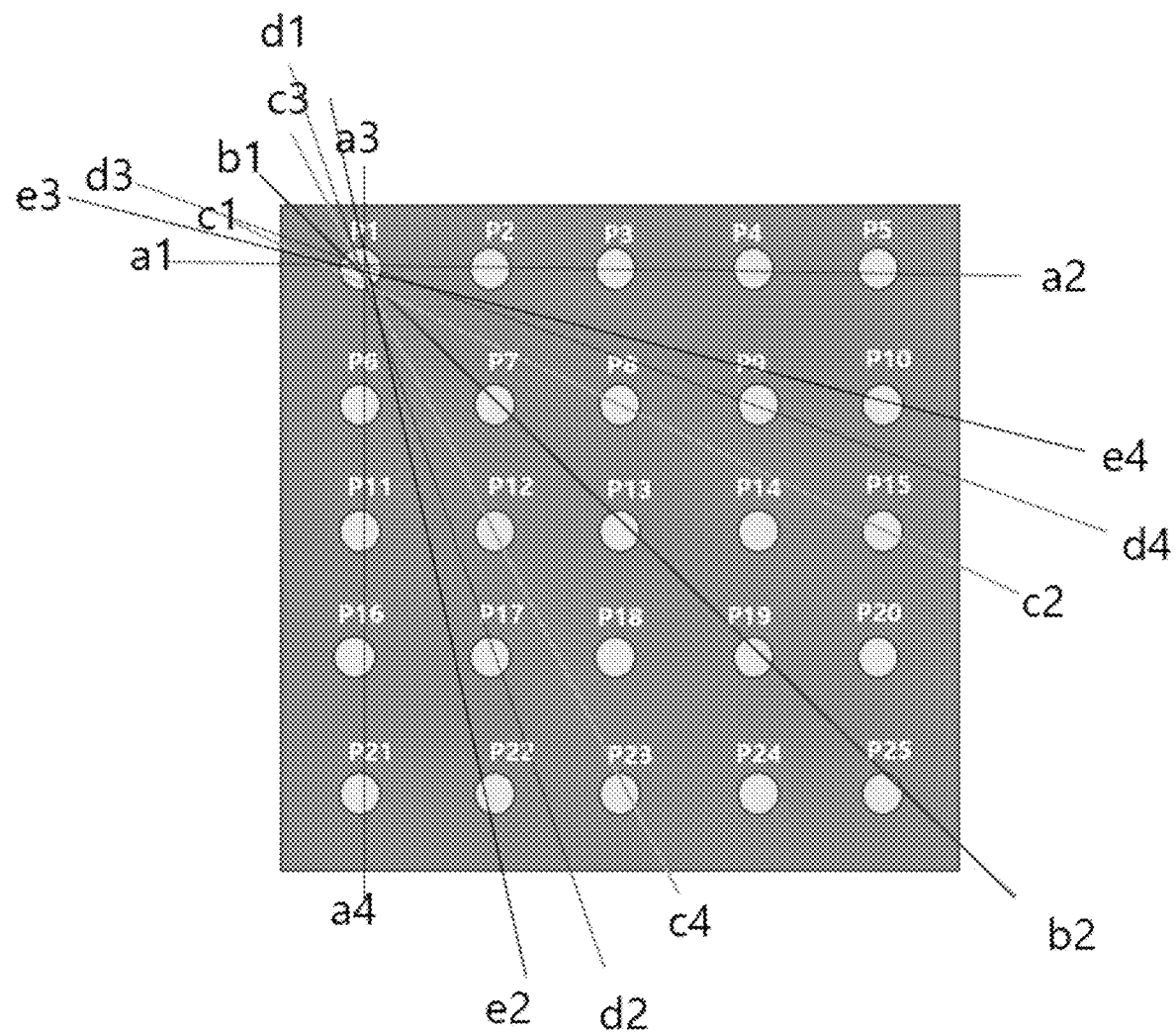
Figure 13:
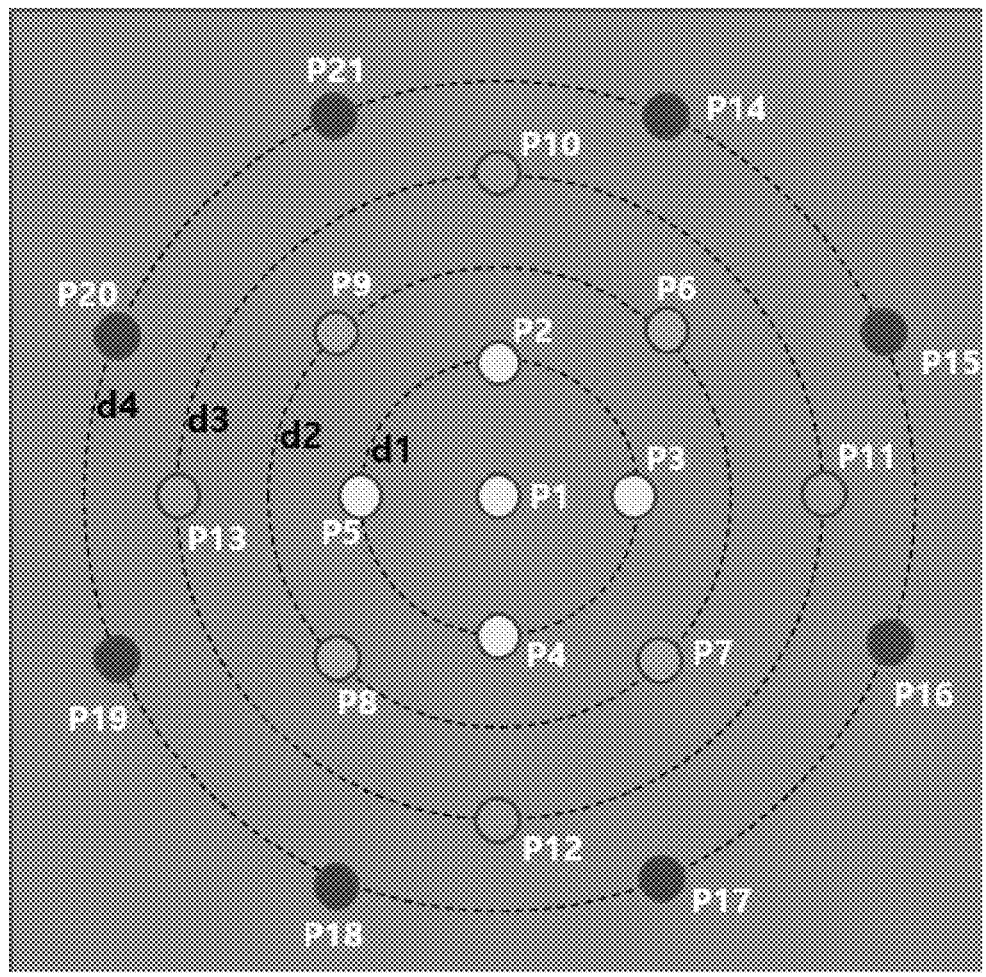

FIG. 10 is a schematic diagram of a bio-signal measuring device having a microelectrode array pattern according to the present invention. FIGS. 11 to 13 show various embodiments of a microelectrode array pattern according to the present invention.

FIG. 10 is a schematic diagram showing 3D-shaped electrodes in the form of an array proposed in the present invention. These 3D-shaped electrodes are only one example, and 2D-shaped array electrodes are also applicable.

FIG. 11 is a schematic diagram illustrating a new measuring method using array-type electrodes proposed in the present invention. As shown in FIG. 9, the conventional measuring method is a method of detecting disease by measuring the capacitance or impedance between two electrodes and detecting a change attributable to the presence or absence of the disease. However, in the present invention, a large number of array-type electrodes are used, various capacitances or impedances are measured between a number of surrounding electrodes, and changes are observed, thereby significantly improving accuracy and reliability.

The present invention is directed to a bio-signal measuring device in which a plurality of microelectrodes 200 is disposed on a substrate 100. In more detail, the present invention is directed to a bio-signal measuring device having a microelectrode array pattern in which one microelectrode, which is a reference electrode, and corresponding electrode groups including other microelectrodes located at different same distances from the reference electrode are set and the measured values of the capacitance or impedance between the reference electrode and the microelectrodes of the corresponding electrode groups are obtained.

The present invention may obtain the average of measured values for each of the corresponding electrode groups.

In the present invention, there may be obtained the average of measured values excluding at least one of the upper and lower limit values of measured values for each of the corresponding electrode groups.

In general, the average of measured values is obtained. However, if an error is expected in the upper or lower limit value, the average of measured values excluding it may be obtained.

The array pattern structure of microelectrodes according to the present invention may be implemented as various embodiments.

In an embodiment, a plurality of microelectrodes 200 may be disposed with the same numbers of microelectrodes arranged in the longitudinal and transverse directions, and a reference electrode may be any one of the plurality of microelectrodes.

In this embodiment, it is preferable that the plurality of microelectrodes 200 be disposed with the same odd numbers of microelectrodes arranged in the longitudinal and transverse directions and the reference electrode be set to a microelectrode located at the center. However, this does not mean that an embodiment in which the plurality of microelectrodes 200 is disposed with the same even numbers of microelectrodes arranged in the longitudinal and transverse directions is excluded from the scope of the present invention.

In another embodiment, a plurality of microelectrodes 200 may be disposed with different numbers of microelectrodes arranged in the longitudinal and transverse directions (not shown), and a reference electrode may be any one of the plurality of microelectrodes 200.

Meanwhile, the "longitudinal direction" and the "transverse direction" used herein are not limited to the horizontal direction and the vertical direction, but are concepts including the diagonal directions.

For example, the microelectrodes may be disposed in the vertical and horizontal directions, the diagonal directions, or random directions as desired. However, a pattern is characterized as being formed such that a plurality of other electrodes at the same distances from a reference electrode is provided.

FIG. 11 shows, as an example, a pattern structure in which 25 microelectrodes are configured in an array form. When P13, which is the central one of the electrodes, is set as a reference electrode, there are a total of 4 microelectrodes P8, P12, P18, and P14 at the shortest same distance from the electrode P13.

In the present invention, microelectrodes located at the same distance from the reference electrode are referred to as a corresponding electrode group. Accordingly, the four microelectrodes located at the shortest same distance are referred to as a first corresponding electrode group.

The first corresponding electrode group includes four microelectrodes P8, P12, P18, and P14 on lines a1-a2 and a3-a4 of FIG. 11, and there are obtained four measured values with respect to the reference electrode.

In this case, in the conventional art, there is one measured value of the capacitance or impedance between two electrodes. In contrast, in the case of the present invention, there are four electrodes closest to the reference electrode, and thus four measured values are present.

Four microelectrodes P7, P9, P17, and P19 at the next shortest same distance from the reference electrode after the same distance to the first corresponding electrode group constitute a second corresponding electrode group. The four microelectrodes are present on lines b1-b2 and b3-b4 of FIG. 11, and there are obtained four measured values with respect to the reference electrode.

Four microelectrodes P3, P11, P15, and P23 at the next shortest same distance from the reference electrode after the same distance to the second corresponding electrode group constitute a third corresponding electrode group. The four microelectrodes are present on lines a1-a2 and a3-a4 of FIG. 11, and there are obtained four measured values with respect to the reference electrode.

Eight microelectrodes P6, P20, P2, P24, P4, P22, P10, and P16 at the next shortest same distance from the reference electrode after the same distance to the third corresponding electrode group constitute a fourth corresponding electrode group. The eight microelectrodes are present on lines c1-c2, c3-c4, c5-c6, and c7-c8 of FIG. 11, and there are obtained eight measured values with respect to the reference electrode.

Four microelectrodes P1, P5, P21, and P25 at the next shortest same distance from the reference electrode after the same distance to the fourth corresponding electrode group constitute a fifth corresponding electrode group. The four microelectrodes are present on lines b1-b2 and b3-b4 of FIG. 11, and there are obtained four measured values with respect to the reference electrode.

In summary, when the electrode P13 is set as the reference electrode, a total of 24 changes in capacitance or impedance between the electrodes may be obtained, and thus a characteristic value having considerably high accuracy and considerably high reliability may be obtained compared to the conventional measuring method.

FIG. 12 shows an embodiment in which, for example, another electrode P1 is set as a reference electrode. In this embodiment, a total of 24 measured values may be obtained by setting corresponding electrode groups ranging from a corresponding electrode group at the shortest same distance to a corresponding electrode group at the longest same distance and measuring changes in capacitance or impedance between electrodes with respect to the reference electrode.

In this manner, the measured values of changes may be obtained between adjacent electrodes at each of the positions of a total of 25 microelectrodes. Accordingly, in the case of 25 electrodes, a total of 300 measured values are obtained at one time. Through this, considerably accurate and reliable measured values may be obtained.

When the number of electrodes is n, the number of measured values that can be measured at one time is $n(n-1)/2$. In the case of 100 electrodes, 4,950 measured values are obtained at one time.

Meanwhile, FIG. 13 shows an embodiment in which a microelectrode array has a concentric pattern structure. As shown in FIG. 13, a plurality of microelectrodes 200 is disposed at the center of a plurality of concentric circles and on the circumferences of the concentric circles, a reference electrode may be a microelectrode disposed at the center of the circles, and corresponding electrode groups may each be microelectrodes disposed on the circumference of each of the concentric circles.

In the case of FIG. 13, four microelectrodes P2, P3, P4, and P5 at the shortest same distance d1 from a reference electrode P1 constitute a first corresponding electrode group.

Four microelectrodes P6, P7, P8, and P9 at the next shortest same distance d2 after the shortest same distance to the first corresponding electrode group d1 constitute a second corresponding electrode group.

Four microelectrodes P10, P11, P12, and P13 at the next shortest same distance d3 after the shortest same distance to the second corresponding electrode group d2 constitute a third corresponding electrode group.

Eight microelectrodes P14, P15, P16, P17, P18, P19, P20, and P21 at the next shortest same distance d4 after the shortest same distance to the third corresponding electrode group d3 constitute a fourth corresponding electrode group.

As presented in the various embodiments, according to the present invention, the distribution of measured values may be represented by a number of measured values, changes between electrodes attributable to the presence of a biomarker or disease may be more accurately compared, and disease may be significantly accurately detected.

Figure 14A:
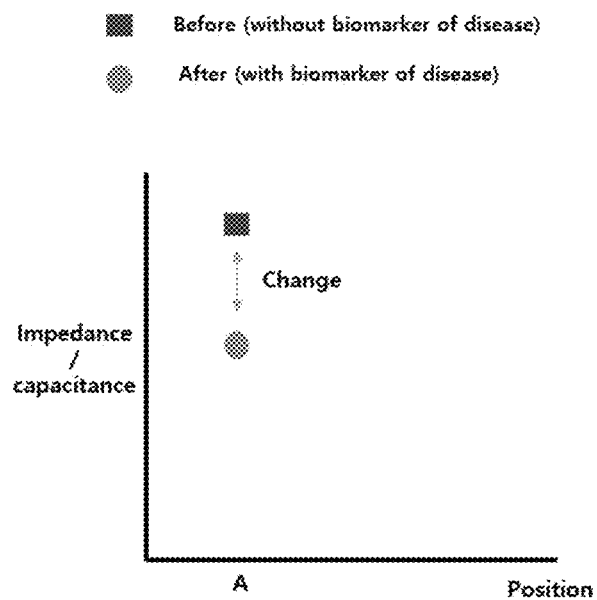
FIG. 14(a) and FIG. 14(b) show data on the comparison of results obtained by measuring a characteristic using a microelectrode array pattern according to the present invention.
Figure 14B:
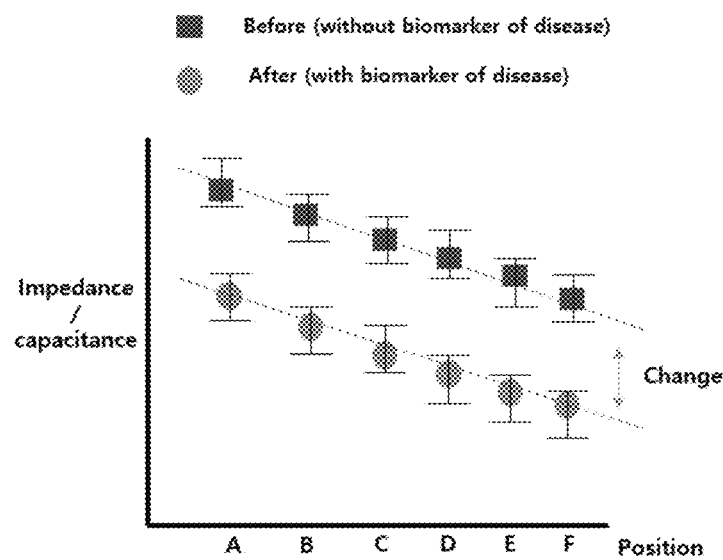

FIG. 14 shows data on the comparison of results obtained by measuring a characteristic by the method proposed in the present invention. FIG. 14(a) shows data measured between two electrodes as in the conventional method. FIG. 14(b) shows measured data obtained using the array electrodes and the simultaneous measurement method proposed in the present invention.

In FIG. 14, red square marks indicate the measured values of impedance or capacitance between electrodes in a reference state without a biomarker or disease. In FIG. 14, blue circular marks indicate measured values in a state with a biomarker or disease. The presence or absence of a disease may be predicted by changes between the two types of measured values.

In the conventional method shown in FIG. 14(a), there are two electrodes, and thus there is only one piece of measured data between the electrodes. In other words, there is one measured value in the reference state and there is one measured change value, and thus only one constant data value may be obtained for the change.

However, since the shape of the electrode and the distribution of a biomarker do not completely match each other in an actual state, there is a limitation to making an accurate diagnosis using only one data change value.

However, in the present invention, since a plurality of array electrodes is used, there are many electrodes (a first corresponding electrode group) located closest to one reference electrode, so that measured values are also obtained as more reliable values by using a plurality of average values.

Furthermore, since the array electrodes are used, there are a number of positions of electrodes (corresponding electrode groups) located at different same distances from a reference electrode, as illustrated in FIGS. 10 to 13, so that average measured values for a plurality of corresponding electrode groups may be obtained in various positions B, C, D, E, and F at the same distances. As a result, the number of parameters compared with the reference state is increased, and thus an accurate diagnosis may be made through more accurate comparison.

In addition, since changes in impedance or capacitance based on individual positions may be represented on a graph, changes may be represented by changes between slopes of curves rather than simple constant changes.

FIG. 14 shows an example in which a measured impedance or capacitance value in a state having a biomarker or disease is decreased compared to a measured impedance or capacitance value in a reference state. However, depending on the type of disease, such a measured value may be increased, in which case the above-described comparison of a change may be applied in the same manner.

Figure 15:
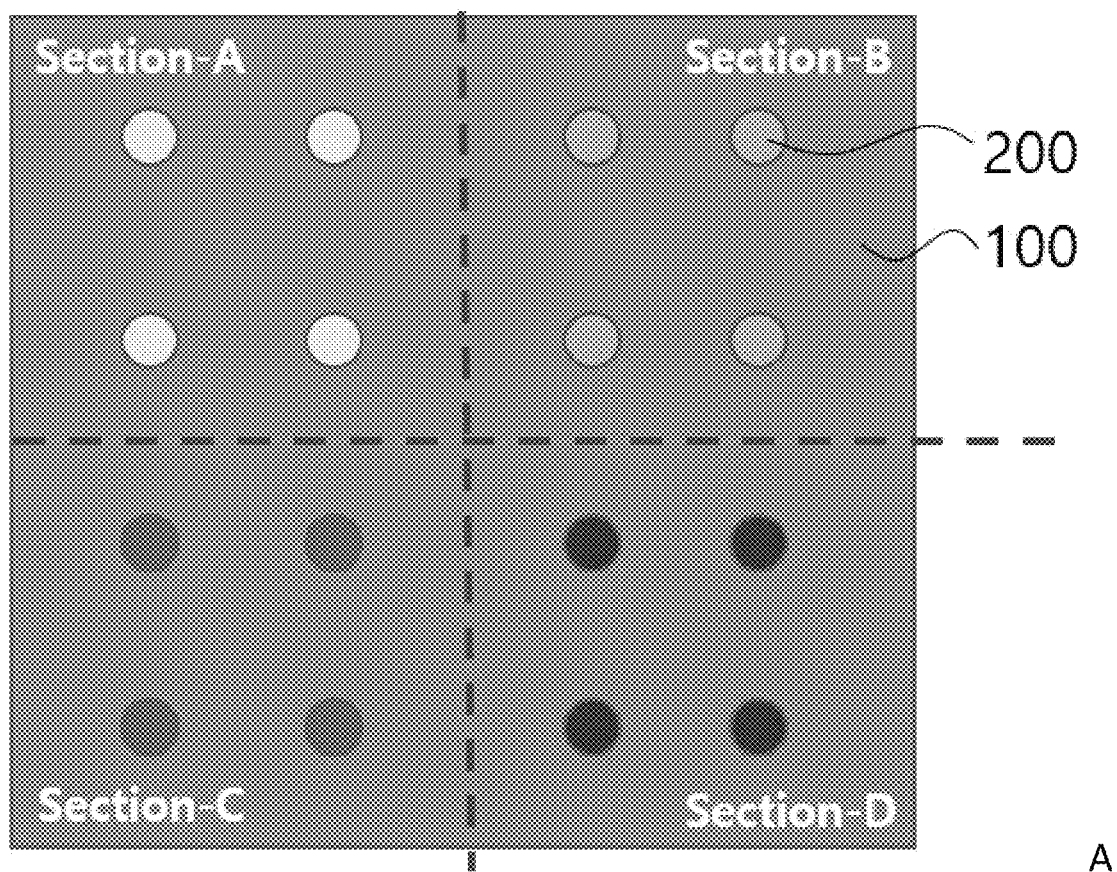
FIG. 15 shows an embodiment in which an array pattern is divided into a plurality of sections in the present invention.

FIG. 15 shows an embodiment in which an array pattern is divided into a plurality of sections in the present invention. More specifically, FIG. 15 is a schematic diagram showing a method of detecting a plurality of diseases at one time rather than one disease in a single array electrode structure.

As described above, a biomarker varies depending on the type of disease. The array electrode structure is divided into a desired number of sections, and the electrode structure or receptors attached to electrodes is or are adjusted to detect different biomarkers in the respective sections, so that various diseases may be detected at one time.

In the embodiment of FIG. 15, an array electrode structure may be divided into four sections A, B, C, and D, and the individual sections may be configured to detect different biomarkers.

Referring to FIG. 15 as an example, when settings are made such that a VEGF biomarker is detected in section A, beta-amyloid is detected in section B, troponin is detected in section C, and glucose is detected in section D, cancer, Alzheimer's, myocardial infarction, and diabetes may all be detected using a single drop of blood.

In addition, in the case of the embodiment of FIG. 15, each of the sections is composed of four electrodes. Accordingly, as described in the embodiments of FIGS. 11 and 12, six pieces of measured data may be obtained for each of the sections. As a result, even when a plurality of diseases is detected through measurement, high accuracy and high reliability may be ensured.

As described above, the bio-signal measuring device according to the present invention may implement an innovative measuring device and method capable of obtaining data having high accuracy and high reliability and detecting various diseases at one time through a single measurement.

Next, a neural signal feedback method according to the present invention will be described. The neural signal feedback method differs from the above-described neural signal feedback system only in the category of the invention, and they have a common invention configuration. Therefore, descriptions of the common technical configurations will be replaced with corresponding descriptions given in conjunction with the above-described feedback system, and the following description will be given with a focus on the sequence of the neural signal feedback method.

FIG. 4 is a flowchart showing a neural signal feedback method using a microelectrode array unit according to the present invention.

The present invention is directed to a neural signal feedback method that may be implemented as a program that is executed by an operation processing means including a computer. In this case, the operation processing means includes an analysis and determination unit.

In step S1 according to the present invention, the microelectrode array unit 10 in which a plurality of microelectrodes is disposed on a substrate and one microelectrode, which is a reference electrode, and corresponding electrode groups including other microelectrodes located at different same distances from the reference electrode are set may measure neural signal values and transmit the measured values to the analysis and determination unit 20 in a state of having been inserted into the human body.

In step S2 according to the present invention, the analysis and determination unit 20 may determine whether to apply electrical stimulation by comparing the measured value with a preset reference value.

In step S3 according to the present invention, the analysis and determination unit 20 may apply electrical stimulation from the microelectrode array unit when, as a result of the comparison of step S2, it is determined that the measured values do not reach the reference value.

In the present invention, steps S1 to S3 may be repeatedly performed until the measured values reach the reference value.

When the measured values reach the reference value in step S2, the analysis and determination unit does not apply electrical stimulation, and a feedback loop is terminated.

In the present invention, the measured neural signal value is preferably an action potential value.

In the present invention, the neural signal value in a state in which an analog signal is changed into a digital signal and the amount of information transmitted and the amount of information received are the same may be set as the reference value.

In the present invention, the electrical stimulation may be applied through each of the microelectrodes.

Next, the present invention may be implemented as a computer program.

In the present specification, hardware includes a process (CPU). More specifically, the method is performed through the interaction between the program and the process in a state in which a computer program including computer instructions for the neural signal feedback method using a microelectrode array unit according to the present invention has been loaded into memory.

The computer program according to the present invention may be implemented as a computer program stored in a computer-readable recording medium in order to be combined with the hardware of a computer and execute the neural signal feedback method using a microelectrode array unit according to the present invention.

The neural signal feedback system and method using a microelectrode array unit according to the present invention have the following advantages:

A first advantage of the present invention is to acquire a large number of highly-accurate measured values through the simple yet diverse microelectrode array pattern structures.

A second advantage of the present invention is to analyze a measured value more accurately by comparing the value converted into a digital signal.

A third advantage of the present invention is to determine whether to apply electrical stimulation through comparison with a reference value in the analysis and determination unit.

A fourth advantage of the present invention is to construct the feedback system that automatically applies electrical stimulation until measured values reach a reference value.

The advantages of the present invention are not limited to those mentioned above, and other advantages that are not mentioned will be clearly understood by those skilled in the art from the foregoing description.

The embodiments described in the present specification and the accompanying drawings are merely illustrative of some of the technical spirits included in the present invention. Therefore, it is obvious that the embodiments disclosed in the present specification are not intended to limit the technical spirit of the present invention, but are intended to illustrate the technical spirit, so that the scope of the technical spirit of the present invention is not limited to these embodiments. Modifications and specific embodiments that can be easily derived by those skilled in the art within the scope of the technical spirits included in the present specification and drawings of the present application should be interpreted as being included in the scope of the present invention.

What is claimed is:

1. A neural signal feedback system, the neural signal feedback system being operated by a program executed by an operation processing means including a computer, the operation processing means including an analysis and determination unit, the neural signal feedback system comprising:
a microelectrode array unit configured such that a plurality of microelectrodes is disposed on a substrate and such that one microelectrode, which is a reference electrode, and corresponding electrode groups including other microelectrodes located at different distances from the reference electrode are set; and
the analysis and determination unit configured to compare neural signal values, measured in the microelectrode array unit, with a preset reference value, and to determine whether to apply electrical stimulation of the microelectrode array unit;
wherein the analysis and determination unit performs re-measurement after application of electrical stimulation, and repeats application of electrical stimulation and measurement until the measured values reach the reference value,
wherein the measurement and the application of electrical stimulation are performed with the individual microelectrodes matched with respective single cells in a one-to-one correspondence,
wherein:
the plurality of microelectrodes disposed on the substrate are divided into a plurality of preset sections; and
receptors that are attached to the microelectrodes of each of the preset sections are adjusted such that the microelectrodes of each of the preset sections detect a different biomarker,
wherein the plurality of microelectrodes are arranged in a pattern of a plurality of concentric circles that are equally spaced and the reference electrode is located at a center of the concentric circles,
wherein a first group of the plurality of microelectrodes are arranged in a cross pattern of which the center of the cross pattern coincides with the center of the concentric circles at which the reference electrode is located and a second group of the plurality of microelectrodes are arranged in longitudinal straight lines and transverse straight lines to be symmetrical about the reference electrode, and
wherein the first group of the plurality of microelectrodes in the cross pattern are not located in the longitudinal straight lines and the transverse straight lines on which the second group of the plurality of microelectrodes are located.

2. The neural signal feedback system of claim 1, wherein the measured neural signal values comprise action potential values.

3. The neural signal feedback system of claim 2, wherein the neural signal values are converted from an analog signal into a digital signal, and are expressed as amounts of information in bits.

4. The neural signal feedback system of claim 1, wherein the analysis and determination unit receives the measured neural signals value via a wireless or wired connection.

5. The neural signal feedback system of claim 1, wherein an average of measured values is obtained for each of the corresponding electrode groups.

6. The neural signal feedback system of claim 1, wherein an average of measured values excluding at least one of upper and lower limit values of measured values for each of the corresponding electrode groups is obtained.

* * * * *